United States Patent
Jones

(10) Patent No.: US 10,292,035 B2
(45) Date of Patent: May 14, 2019

(54) IDENTIFICATION BRACELET AND METHODS

(71) Applicant: Gail Yvette Jones, District Heights, MD (US)

(72) Inventor: Gail Yvette Jones, District Heights, MD (US)

(*) Notice: Subject to any disclaimer, the term of this patent is extended or adjusted under 35 U.S.C. 154(b) by 0 days.

(21) Appl. No.: 15/914,259

(22) Filed: Mar. 7, 2018

(65) Prior Publication Data

US 2018/0262898 A1 Sep. 13, 2018

Related U.S. Application Data

(60) Provisional application No. 62/468,324, filed on Mar. 7, 2017.

(51) Int. Cl.
| | | |
|---|---|---|
| *H04W 4/90* | (2018.01) | |
| *H04W 4/029* | (2018.01) | |
| *H04B 1/3827* | (2015.01) | |
| *A61B 5/024* | (2006.01) | |
| *A61B 5/00* | (2006.01) | |

(52) U.S. Cl.
CPC ............ *H04W 4/90* (2018.02); *A61B 5/0022* (2013.01); *A61B 5/02438* (2013.01); *A61B 5/7435* (2013.01); *H04B 1/385* (2013.01); *H04W 4/029* (2018.02); *A61B 2560/0214* (2013.01); *A61B 2560/0271* (2013.01); *A61B 2560/0493* (2013.01); *H04B 2001/3861* (2013.01)

(58) Field of Classification Search
CPC ..... H04W 4/22; H04W 76/007; H04W 64/00; H04W 4/02; H04W 88/02; H04L 29/0865; H04M 1/72519; H04M 1/72522; G06Q 10/08; H07C 9/00111; H08B 21/0269
USPC ............ 455/404.2, 456.6, 550.1; 340/359.13
See application file for complete search history.

(56) References Cited

U.S. PATENT DOCUMENTS

| | | | | |
|---|---|---|---|---|
| 7,315,242 | B2* | 1/2008 | Eisenman | B60R 25/1003 340/426.1 |
| 2007/0249322 | A1* | 10/2007 | Benco | G06F 21/88 455/410 |
| 2014/0148128 | A1* | 5/2014 | Di | H04W 12/06 455/411 |
| 2014/0213214 | A1* | 7/2014 | Reis | H04W 4/02 455/404.2 |
| 2015/0269824 | A1* | 9/2015 | Zhang | G08B 21/0438 340/539.12 |
| 2015/0269826 | A1* | 9/2015 | Zhang | G08B 21/0446 340/539.12 |
| 2017/0085417 | A1* | 3/2017 | O'Reirdan | H04L 41/0668 |
| 2017/0202180 | A1* | 7/2017 | Yang | A01K 11/008 |
| 2017/0353833 | A1* | 12/2017 | de Barros Chapiewski | H04W 4/023 |
| 2018/0054721 | A1* | 2/2018 | Choe | H04W 4/90 |

* cited by examiner

*Primary Examiner* — Danh C Le
(74) *Attorney, Agent, or Firm* — Duane Morris LLP

(57) ABSTRACT

The embodiments described herein provide an apparatus adapted to be coupled to the body of a user. The apparatus includes a transceiver and a processor configured to determine the user's location. The processor may make this determination based, at least in part, on a plurality of signals received via the transceiver. The processor may then determine that the user is lost and transmit, via the transceiver, a distress signal including the location of the user.

16 Claims, 5 Drawing Sheets

IDENTIFICATION BRACELET AND METHODS

CROSS-REFERENCE TO RELATED APPLICATIONS

This application claims the benefit of U.S. Provisional Patent Application No. 62/468,324, filed Mar. 7, 2017, and entitled "Amber Alert ID Band," which is incorporated herein in its entirety by reference.

BACKGROUND

Disorders that cause memory loss affect millions of people. Dementia and alzheimers are two examples of such disorders that can affect a person's memory. Such people are susceptible to forgetting familiar surroundings, or even their own address and can become lost and/or unable to help themselves very quickly. In addition, certain individuals may have a disability, and/or may have special needs that render them unable to care for themselves. If these individuals become separated from their caretaker (e.g. during an outing in an unfamiliar environment) they may be unable to find their way back to their caretaker or any other safe place and may be stranded. Further, small children are prone to being accidentally separated from their parents and lost, especially in places such as amusement parks and camping sites. Thus, such people can be very vulnerable, especially in the case of the elderly or children.

Thus, there is a need for a way to monitor and keep track of such individuals, and allow them to call for help and be located when they are lost.

The foregoing examples of the related art and limitations related therewith are intended to be illustrative and not exclusive. Other limitations of the related art will become apparent upon a reading of the specification and a study of the drawings.

SUMMARY OF THE INVENTION

The embodiments described herein provide an apparatus adapted to be coupled to the body of a user. The apparatus includes a transceiver and a processor configured to determine the user's location. The processor may make this determination based, at least in part, on a plurality of GPS signals received via the transceiver. The processor may then determine that the user is lost and transmit, via the transceiver, a distress signal including the location of the user.

In other embodiments, a system is provided, the system including an apparatus adapted to be coupled to the body of a user, and a charging case adapted to be coupled to the body of the charging case. The charging case may provide power to the apparatus. The apparatus includes a transceiver and a processor configured to determine the user's location. The processor may make this determination based, at least in part, on a plurality of GPS signals received via the transceiver. The processor may then determine that the user is lost and transmit, via the transceiver, a distress signal including the location of the user.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
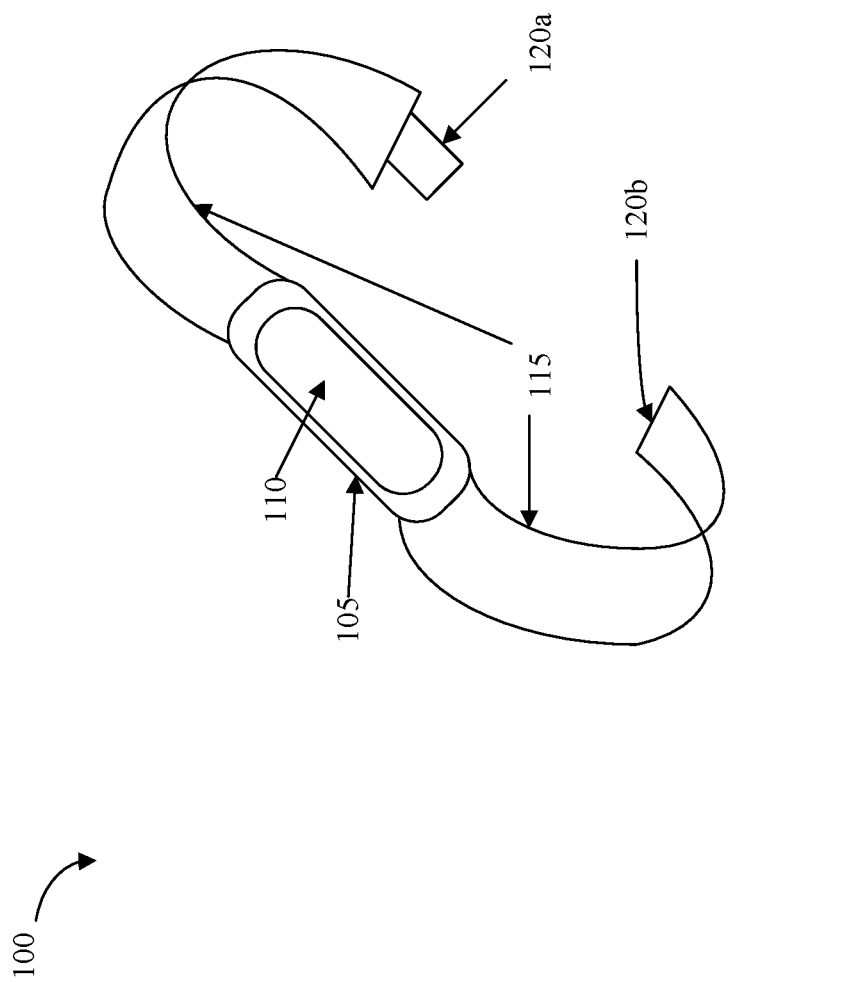
FIG. 1 is a perspective view of a wearable device, in accordance with some embodiments of the present disclosure.

The following disclosure provides many different embodiments, or examples, for implementing different features of the subject matter. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Aspects of the present disclosure contemplate a wearable device that may fit securely to the user and continuously track the user's location. If the user becomes lost, or is unable to find their way, the device may alert emergency aid services and transmit the user's location, along with other information, to such aid services and/or to a trusted third party. The wearable device may also store the user's personal information which may be accessed by the user when required.

FIG. 1 illustrates an ID bracelet 100 for monitoring the location of a user. The ID bracelet 100 may include a body 105, a touch screen display 110, a strap 115, and a locking mechanism 120. The body 105 may be made of stainless steel or any other suitable material and may also be water proof. The strap 115 may be made of rubber, canvas, or any other suitable material and may also be water proof. The strap 115 may include a male connector 120*a* at one end, and a female connector 120*b* at the other. The ID bracelet 100 may be locked in place, on a users wrist for example, by inserting the male connector 120*a* into the female connector 120*b*. Upon insertion, the male connector 120*a* may automatically be locked in place. In some embodiments, a passcode must be entered on the touch sensitive display 110 in order to lock the male connector 120*a* into place, as discussed in more detail herein. Once locked into place, the male connector 120*a* cannot be disconnected from the female connector 120*b* until the passcode is entered on the touch sensitive display 110.

The touch sensitive display 110 may display a variety of icons or graphics, each corresponding to a particular functionality. A particular function may be selected by pressing on the corresponding icon or graphic. For example, touch sensitive display 110 may display a distress (SOS) icon, an unlock icon, and a personal information display icon, among others. Upon receiving a user selection, the ID bracelet 100 may perform the corresponding function, as described in more detail herein.

For example, upon receiving a user selection of the distress icon, the ID bracelet 100 may send a distress signal to an emergency service (e.g. fire and rescue, ambulance) as discussed in more detail herein. In another example, upon receiving a user selection of an unlock icon, the ID bracelet 100 may request that the user input a passcode. Upon receiving the correct passcode via the touch sensitive display 110, the ID bracelet 100 may unlock the male connector 120a from the female connector 120b.

Figure 2:
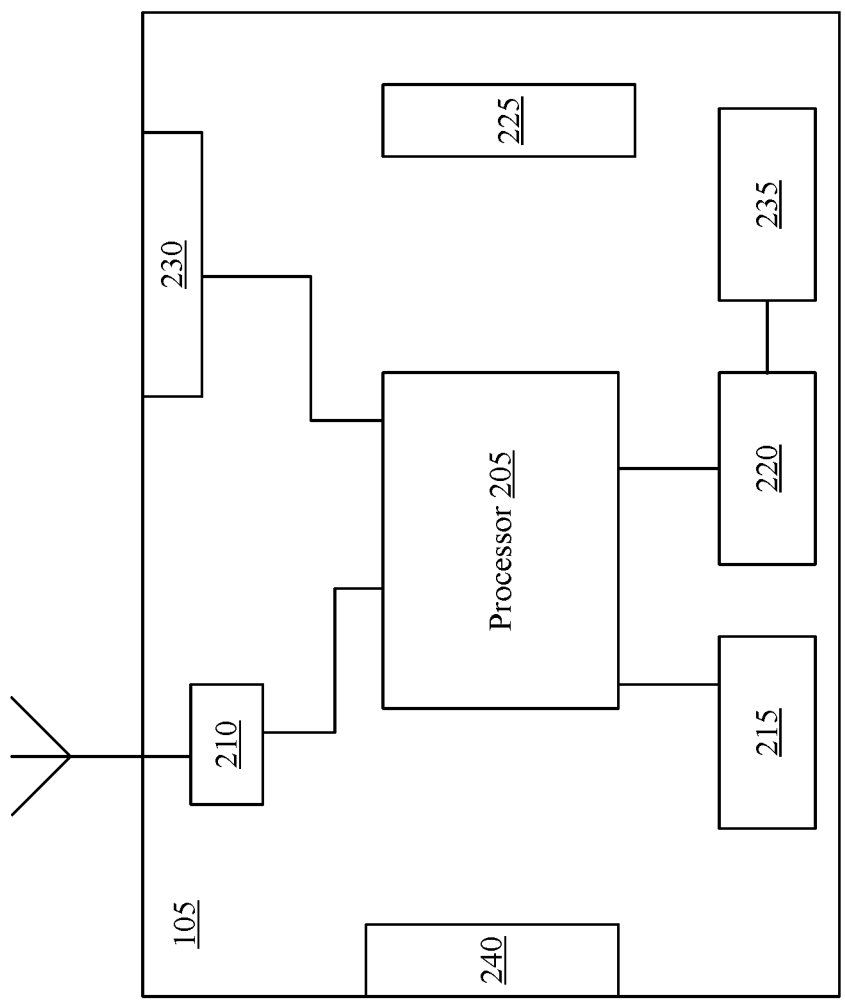
FIG. 2 is a block diagram of a wearable device in accordance with some embodiments of the present disclosure.

FIG. 2 illustrates a hardware block diagram of the body 105 of ID bracelet 100 as illustrated in FIG. 1. The body 105 may include a processor 205, a transceiver 210, a heart rate sensor 215, solar cell 220, memory 225, a touch screen interface 230, a battery 235, and a microphone 240. Although illustrated as having an antenna that protrudes from the body 105, in some embodiments the antenna of transceiver 210 may be integrated within the body 105.

Memory 225 may be any non-transitory computer readable medium and may contain instructions for performing the functions of the processor 205 as described below with respect to FIG. 2. Memory 225 may also contain a database (not shown) including the personal information of the user as well as other information. For example, memory 225 may store the user's name, address, and contact information among other details. In addition, memory 225 may store contact information of the user's trusted third parties (e.g., family, close friends). In some embodiments, the memory 225 may also store the user's medical information.

The body 105 may receive signals from a plurality of satellites (not shown) via the transceiver 210 at regular intervals. More specifically, each of the plurality of satellites may transmit signals carrying information regarding their current time and position at regular intervals and these signals may be received by the body 105 via transceiver 210. Upon receiving the signals, transceiver 210 may route the signals to the processor 205. Processor 205 may solve a set of equations to determine the current position of body 105 (and thus, the user) based on the signals received from each of the plurality of satellites. In some embodiments, the body 105 may be equipped with cellular or wireless internet capabilities and the process of determining the user's position may be enhanced through the use of such cellular and/or wireless internet capabilities as is known in the art.

In some embodiments, processor 205 may compare the calculated position to a geographical range or boundary within which the user must be, and if the user is determined as being outside this range, processor 205 may transmit a distress signal to emergency aid services and/or a trusted third party of the user. Processor 205 may transmit the distress signal via transceiver 210.

In some embodiments, the user may indicate they are lost by inputting a command to the body 105. For example, the user may press an icon on the touch screen display (shown in FIG. 1) indicating that they are lost. The touch screen interface 230 may route the command to processor 205, which may request assistance as described above. In other embodiments, the user may input the command by speaking into the microphone 240 (e.g. by saying "I am lost"). Processor 205 may receive the signal from the microphone 240 and may request assistance as described above In some embodiments, processor 205 may also monitor the user's heart rate by polling the heart rate sensor 215 at regular intervals. The heart rate sensor 215 may be any suitable sensor for determining a user's heart rate as is known in the art. The heart rate sensor 215 may determine the user's heart rate based on signals acquired from the area where the body 105 makes contact with the user. When processor 205 polls the user's heart rate, it may compare the heart rate to a pre-defined maximum heart rate criteria. In some embodiments, if the user's heart rate exceeds the threshold, then processor 205 may alert emergency services and/or a trusted third party of the user by transmitting a distress signal as discussed above. In other embodiments, if the processor 205 determines that the user's heart rate is above the predefined maximum heart rate criteria, then it may wait until the user provides a voice command (as discussed above) requesting assistance before transmitting the distress signal.

The user may also wish to retrieve their personal details stored in memory 225, to provide such information to emergency aid workers, for example. Thus, the user may input a command to the body 105 (e.g. by selecting an appropriate icon on the touch screen display as described above), and upon receiving the command from the touch screen interface 230, processor 205 may retrieve the user's personal details from memory 225 and transmit them to touch screen interface 230 for display on the touch screen display (shown in FIG. 1).

In some embodiments, solar cell 220 may convert energy from sunlight into electricity to provide power to body 105. In some embodiments, solar cell 220 may be configured to recharge the battery 235 when the charge level of battery 235 falls below a predefined threshold. Once the charge level of battery 235 reaches a second predefined charge level, solar cell 220 may cease operation. In other embodiments, solar cell 220 may be configured to provide power directly to the components of body 200 when the charge level of battery 235 falls below a predefined threshold.

In some embodiments, processor 205 may detect that the locking mechanism of the ID bracelet has been engaged (e.g. the male connector 120a has been inserted into the female connector 120b). Upon detecting that the user has requested to unlock the ID bracelet 100 (e.g. when the user has selected the unlock icon on the touch screen display), processor 205 may request the user to input the passcode. Upon receiving the passcode via touch screen interface 230, processor 205 may send a signal to the female connector 120b instructing it to disengage the locking mechanism.

Figure 3:
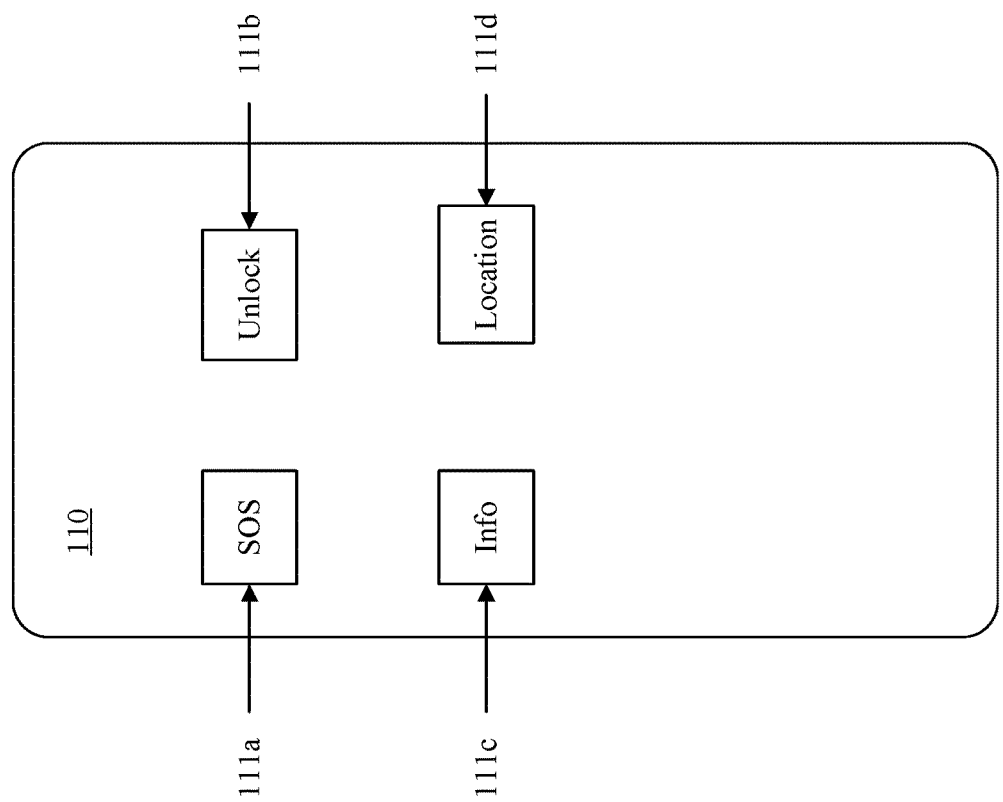
FIG. 3 illustrates a touch sensitive display providing various options to a user in accordance with some embodiments of the present disclosure.

FIG. 3 illustrates a sample front view of the touch screen display 110 of ID bracelet 100 illustrated in FIG. 1. The touch screen display 110 may display a number of selectable icons 111a-111d, where each icon corresponds to a particular function of the ID bracelet. It should be noted that the touch screen display 110 is illustrated as having 4 icons for ease of illustration, and touch screen display 110 may have any appropriate number of icons.

Figure 4:
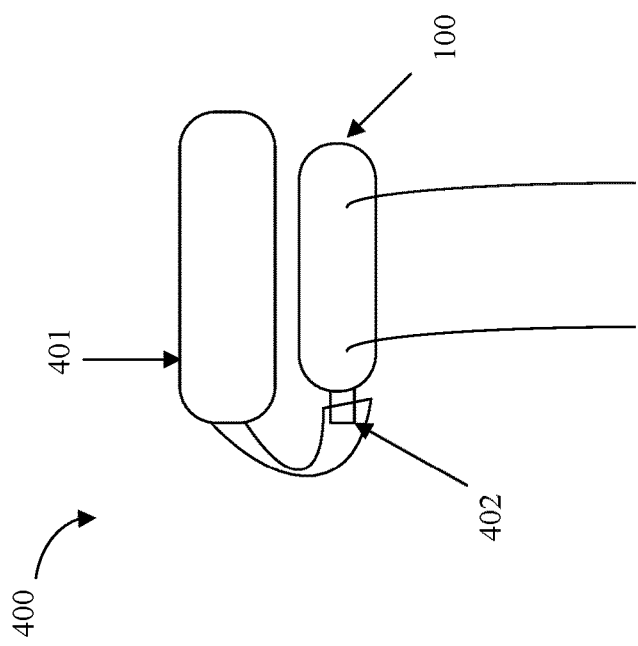
FIG. 4 illustrates a charging case attached to the wearable device of FIG. 1, in accordance with some embodiments of the present disclosure.

FIG. 4 illustrates the ID bracelet 100 of FIG. 1 with charging case 400 attached to it. The charging case 400 may include a body 401 having a rechargeable battery (not shown) within. The body 401 may comprise at least in part, a clear material to allow the touch screen display 110 of the ID bracelet 100 to be seen through it. The body 401 may be configured to fit securely over the body of the ID bracelet 100. The charging case 400 may include a charging mechanism 402 that is configured to operatively couple to the ID bracelet 100 so that power may be transferred from the battery of charging case 400 to the ID bracelet 100. The charging mechanism 402 may be any suitable mechanism for transferring power such as USB-C, USB-A, micro USB, or any other suitable power transfer mechanism. In this way, the charging case 400 may provide power to the ID bracelet 100, allowing the ID bracelet 100 to conserve its own power. In some embodiments, the charging case 400 may be configured to supply power to the ID bracelet 100 only upon detecting that the ID bracelet 100's power level has dropped below a predefined threshold. Similarly, charge mechanism 402 may allow the rechargeable battery of charging case 400 to be recharged (e.g. via an electrical outlet) using any suitable adapter.

Figure 5:
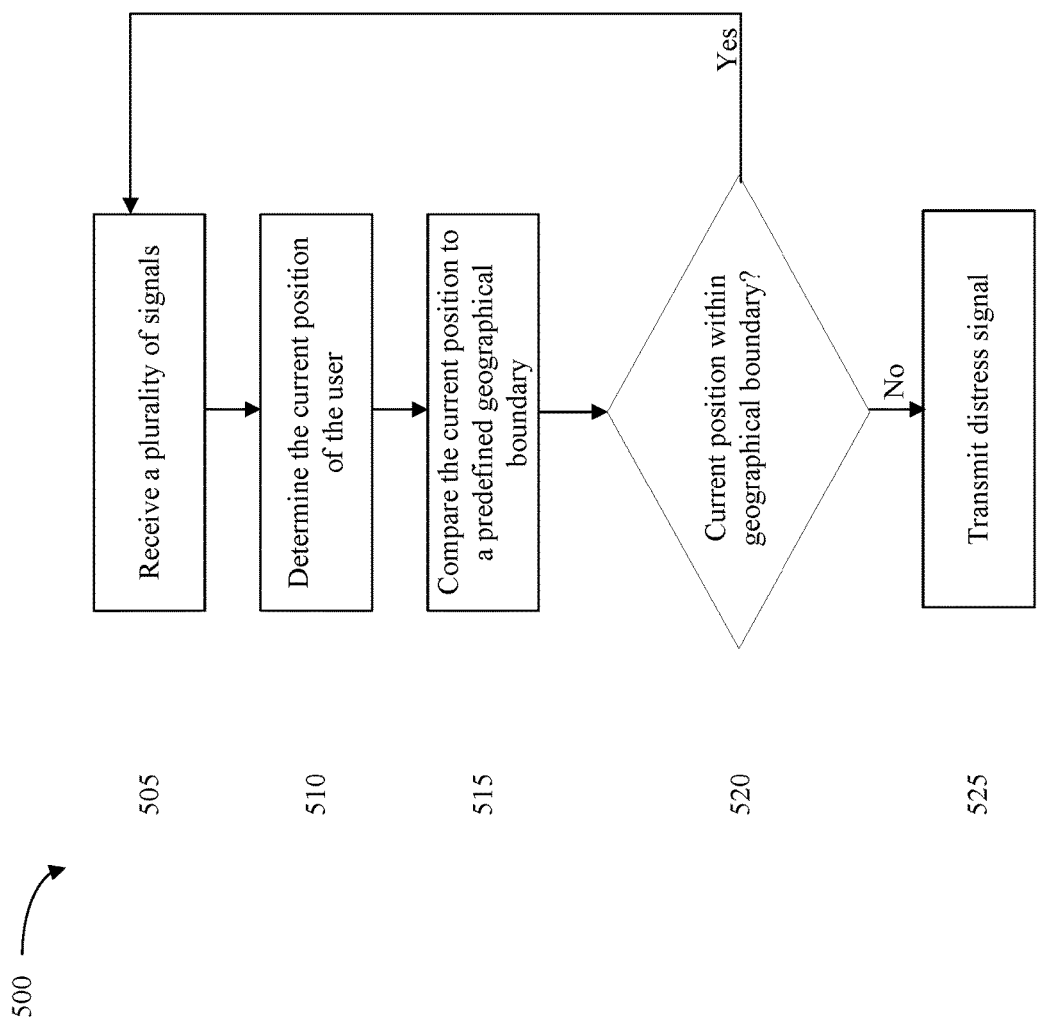
FIG. 5 illustrates a method, in accordance with some embodiments of the present disclosure.

FIG. 5 illustrates a flow diagram of a method 500, in accordance with some embodiments of the present disclosure. Method 500 may be performed by the ID bracelet 100 of FIG. 1, for example. At 505, ID bracelet 505 may receive signals from a plurality of satellites (not shown) at regular intervals. More specifically, each of the plurality of satellites may transmit one or more signals carrying information regarding their current time and position at regular intervals and these signals may be received by ID bracelet 100. At 510, upon receiving the signals, ID bracelet 100 may solve a set of equations to determine the current position of the user based on the signals received from each of the plurality of satellites. In some embodiments, the ID bracelet 100 may be equipped with cellular or wireless internet capabilities and the process of determining the user's position may be enhanced through the use of such cellular and/or wireless internet capabilities as is known in the art.

At 515, ID bracelet 100 may compare the calculated position to a geographical range or boundary within which the user must be. At 520, if the user is determined as being outside this range, ID bracelet 100 may transmit a distress signal to emergency aid services and/or a trusted third party of the user (525). Otherwise, the ID bracelet may continue monitoring the user's position at regular intervals (505).

The foregoing description of various embodiments of the claimed subject matter has been provided for the purposes of illustration and description. It is not intended to be exhaustive or to limit the claimed subject matter to the precise forms disclosed. Many modifications and variations will be apparent to the practitioner skilled in the art. Particularly, while the concept "component" is used in the embodiments of the systems and methods described above, it will be evident that such concept can be interchangeably used with equivalent concepts such as, class, method, type, interface, module, object model, and other suitable concepts. Embodiments were chosen and described in order to best describe the principles of the invention and its practical application, thereby enabling others skilled in the relevant art to understand the claimed subject matter, the various embodiments and with various modifications that are suited to the particular use contemplated.

What is claimed is:

1. An apparatus configured to couple to at least a portion of a body of a user, the apparatus comprising:
a heart rate sensor configured to detect the user's heart rate;
a transceiver positioned proximate to at least the portion of the body of the user, wherein the transceiver is configured to receive a plurality of signals, wherein each of the plurality of signals is received from a respective satellite and indicates a location of the respective satellite; and
a processor configured to be communicatively coupled to the transceiver, wherein the processor is configured to:
receive the plurality of signals from the transceiver;
determine the user's location based, at least in part, on the plurality of signals;
identify whether the user is lost based on (i) the determined location and (ii) whether the user's heart rate, detected by said heart rate sensor, is above a predefined threshold; and
transmit, via the transceiver, at least one distress signal to emergency aid services when the user is identified as being lost, wherein the distress signal includes a representation of the location of the user.

2. The apparatus of claim 1, wherein identifying whether the user is lost comprises determining if the user's location is outside a predefined geographical boundary.

3. The apparatus of claim 1 further comprising a microphone and wherein determining whether the user is lost further comprises detecting, via the microphone, a voice command from the user indicating that assistance is required.

4. An apparatus configured to couple to at least a portion of a body of a user, the apparatus comprising:
a touch screen display configured to present each function of the apparatus as a selectable icon including a male connector and a female connector configured to receive the male connector and lock the male connector in place;
a transceiver positioned proximate to at least the portion of the body of the user, wherein the transceiver is configured to receive a plurality of signals, wherein each of the plurality of signals is received from a respective satellite and indicates a location of the respective satellite; and
a processor configured to be communicatively coupled to the transceiver, wherein the processor is configured to:
receive the plurality of signals from the transceiver;
determine the user's location based, at least in part, on the plurality of signals;
identify whether the user is lost based on the determined location; and
transmit, via the transceiver, at least one distress signal to emergency aid services when the user is identified as being lost, wherein the distress signal includes a representation of the location of the user.

5. The apparatus of claim 4 further configured to display the user's personal information on the touch screen display in response to selection of a user information icon.

6. The apparatus of claim 4, wherein the processor is further configured to instruct the female connector to unlock the male connector in response to receiving a preset code via the touch screen display.

7. An apparatus configured to couple to at least a portion of a body of a user, the apparatus comprising:
a battery;
a solar cell configured to provide power to the apparatus when a charge level of the battery falls below a predefined threshold;
a transceiver positioned proximate to at least the portion of the body of the user, wherein the transceiver is configured to receive a plurality of signals, wherein each of the plurality of signals is received from a respective satellite and indicates a location of the respective satellite; and
a processor configured to be communicatively coupled to the transceiver, wherein the processor is configured to:
receive the plurality of signals from the transceiver;
determine the user's location based, at least in part, on the plurality of signals;
identify whether the user is lost based on; and
transmit, via the transceiver, at least one distress signal to emergency aid services when the user is identified as being lost, wherein the distress signal includes a representation of the location of the user.

8. The apparatus of claim 7, wherein providing power to the apparatus comprises recharging the battery until the charge level of the battery reaches a second predefined threshold.

9. The apparatus of claim 7, wherein providing power to the apparatus comprises providing power to each component of the apparatus directly.

10. A system comprising:
   an apparatus configured to be coupled to the body of a user, the apparatus comprising:
   a heart rate sensor configured to detect the user's heart rate;
   a transceiver positioned proximate to at least the portion of the body of the user, wherein the transceiver is configured to receive a plurality of signals, wherein each of the plurality of signals is received from a respective satellite and indicates a location of the respective satellite; and
   a processor configured to be communicatively coupled to the transceiver, wherein the processor is configured to:
   receive the plurality of signals from the transceiver;
   determine the user's location based, at least in part, on the plurality of signals;
   identify whether the user is lost based on (i) the determined location and (ii) whether the user's heart rate, detected by said heart rate sensor, is above a predefined threshold; and
   transmit, via the transceiver, at least one distress signal to emergency aid services when the user is identified as being lost, wherein the distress signal includes a representation of the location of the user; and
   a case configured to be coupled to the apparatus and provide power to the apparatus.

11. The system of claim 10, wherein the apparatus further comprises a battery and wherein the case is configured to provide power to the apparatus in response to determining that a charge level of the battery is below a predefined threshold.

12. The system of claim 10, wherein determining whether the user is lost comprises determining whether the user's location is outside a predefined geographical boundary.

13. The system of claim 10 wherein the apparatus further comprises a microphone and wherein determining whether the user is lost further comprises detecting, via the microphone, a voice command from the user indicating that assistance is required.

14. The system of claim 10, wherein the case comprises:
   a housing having a rechargeable battery; and
   a charging mechanism configured to supply power from the rechargeable battery to the apparatus.

15. The system of claim 11, wherein providing power to the apparatus comprises recharging the battery to a second predefined threshold.

16. A method of monitoring a user's location, the method comprising:
   sensing a user's heart rate;
   receiving, via a transceiver, a plurality of signals, wherein each of the plurality of signals is received from a respective satellite and indicates a location of the respective satellite;
   transmitting the plurality of signals from the transceiver to a processor that is communicatively coupled to the transceiver;
   determining the user's location based, at least in part, on the plurality of signals via the processor;
   identifying whether the user is lost based on (i) the determined location via the processor and (ii) whether the user's heart rate is above a predefined threshold; and
   transmitting, via the transceiver, at least one distress signal to emergency aid services when the user is identified as being lost, wherein the distress signal includes a representation of the location of the user.

* * * * *